United States Patent
Frits et al.

(10) Patent No.: US 10,398,885 B2
(45) Date of Patent: Sep. 3, 2019

(54) MICRONEEDLE ARRAY AND METHOD OF USE

(71) Applicant: 3M INNOVATIVE PROPERTIES COMPANY, Saint Paul, MN (US)

(72) Inventors: Michael J. Frits, Lake Elmo, MN (US); Craig S. Moeckly, White Bear Lake, MN (US); Daniel H. Berg, Saint Paul, MN (US); Jerome E. Gysbers, Minneapolis, MN (US); Ryan Patrick Simmers, Fargo, ND (US)

(73) Assignee: 3M Innovative Properties Company, St. Paul, MN (US)

( * ) Notice: Subject to any disclaimer, the term of this patent is extended or adjusted under 35 U.S.C. 154(b) by 40 days.

(21) Appl. No.: 15/545,029

(22) PCT Filed: Jan. 19, 2016

(86) PCT No.: PCT/US2016/013820
§ 371 (c)(1),
(2) Date: Jul. 20, 2017

(87) PCT Pub. No.: WO2016/118459
PCT Pub. Date: Jul. 28, 2016

(65) Prior Publication Data
US 2018/0008807 A1    Jan. 11, 2018

Related U.S. Application Data

(60) Provisional application No. 62/105,987, filed on Jan. 21, 2015.

(51) Int. Cl.
*A61B 5/15*    (2006.01)
*A61M 37/00*   (2006.01)

(52) U.S. Cl.
CPC ... *A61M 37/0015* (2013.01); *A61B 5/150022* (2013.01); *A61B 5/150396* (2013.01);
(Continued)

(58) Field of Classification Search
CPC ......... A61M 37/0015; A61B 5/150404; A61B 5/150984
(Continued)

(56) References Cited

U.S. PATENT DOCUMENTS

| 6,091,975 A | 7/2000 | Daddona et al. |
| 6,313,612 B1 | 11/2001 | Sherman et al. |

(Continued)

FOREIGN PATENT DOCUMENTS

| DE | 10 2008 052 749 | 5/2010 |
| JP | 2007-190112 | 8/2007 |

(Continued)

*Primary Examiner* — Bhisma Mehta
*Assistant Examiner* — Nidah M Hussain

(57) ABSTRACT

An article (100) comprising at least one microneedle (160) is provided. The article comprises a first side (112) and a second side (114) opposite the first side. The first side comprises a central cavity portion (120) and a platform portion (130), with at least one microneedle extending therefrom, wherein the platform portion is not coplanar with the central cavity portion. The platform portion substantially surrounds the central cavity portion. The at least one microneedle comprises a body comprising an outer surface (163); a base segment (166) having a base (162) and a first shape; a tip segment (168) having a tip and a second shape, wherein the second shape is distinct from the first shape; a transition plane (167) that delineates the base segment and the tip segment; and a central axis (180). Methods of using the article are also provided.

18 Claims, 7 Drawing Sheets

(52) U.S. Cl.
CPC ... *A61B 5/150404* (2013.01); *A61B 5/150984* (2013.01); *A61M 2037/003* (2013.01); *A61M 2037/0023* (2013.01); *A61M 2037/0053* (2013.01); *A61M 2037/0061* (2013.01)

(58) Field of Classification Search
USPC ........................................................ 604/506
See application file for complete search history.

(56) References Cited

U.S. PATENT DOCUMENTS

| | | | |
|---|---|---|---|
| 6,379,324 | B1 | 4/2002 | Gartstein et al. |
| 6,558,361 | B1 | 5/2003 | Yeshurun |
| 7,648,484 | B2 | 1/2010 | Yeshurun et al. |
| 8,088,321 | B2 | 1/2012 | Ferguson et al. |
| 9,119,945 | B2 * | 9/2015 | Simons ............. A61M 37/0015 |
| 2005/0261631 | A1 | 11/2005 | Clarke et al. |
| 2011/0046556 | A1 | 2/2011 | Kraft |
| 2011/0172609 | A1 * | 7/2011 | Moga ................ A61M 5/14224 604/272 |
| 2011/0213335 | A1 | 9/2011 | Burton et al. |
| 2012/0041337 | A1 | 2/2012 | Ferguson et al. |
| 2012/0078189 | A1 | 3/2012 | Ogawa et al. |
| 2012/0123387 | A1 | 5/2012 | Gonzalez et al. |
| 2012/0258284 | A1 | 10/2012 | Rendon |
| 2016/0136406 | A1 * | 5/2016 | Berry ................. B29C 45/2626 604/506 |
| 2017/0173316 | A1 * | 6/2017 | Syrek ............... A61M 37/0015 |
| 2018/0008807 | A1 * | 1/2018 | Frits ................ A61M 37/0015 |

FOREIGN PATENT DOCUMENTS

| | | |
|---|---|---|
| WO | WO 2012/074576 | 6/2012 |
| WO | WO 2012/122162 | 9/2012 |
| WO | WO 2013/053022 | 4/2013 |
| WO | WO 2014/099404 | 6/2014 |
| WO | WO 2014/105458 | 7/2014 |
| WO | WO 2014/193725 | 12/2014 |
| WO | WO 2015/009523 | 1/2015 |
| WO | WO 2015/009524 | 1/2015 |

* cited by examiner

MICRONEEDLE ARRAY AND METHOD OF USE

CROSS REFERENCE TO RELATED APPLICATIONS

This application is a national stage filing under 35 U.S.C. 371 of PCT/US2016/013820, filed Jan. 19, 2016, which claims the benefit of U.S. Provisional Application No. 62/105,987, filed Jan. 21, 2015, the disclosure of which is incorporated by reference in its/their entirety herein.

BACKGROUND

Transdermal and topical drug delivery can be used for therapeutic treatment, but the number of molecules that can be effectively delivered using these routes can be limited by the barrier properties of skin. The main barrier to transport of molecules through the skin is the stratum corneum (the outermost layer of the skin).

A number of different skin treatment methods have been proposed in order to increase the permeability or porosity of the outermost skin layers, such as the stratum corneum, thus enhancing drug delivery through or into those layers. The stratum corneum is a complex structure of compact keratinized cell remnants separated by lipid domains. The stratum corneum is formed of keratinocytes, which comprise the majority of epidermal cells that lose their nuclei and become corneocytes. These dead cells comprise the stratum corneum, which has a thickness of only about 10-30 microns and protects the body from invasion by exogenous substances and the outward migration of endogenous fluids and dissolved molecules. Various skin treatment methods include the use of microneedles, laser ablation, RF ablation, heat ablation, sonophoresis, iontophoresis, or a combination thereof.

Devices including arrays of relatively small structures, sometimes referred to as microneedles or micro-pins, have been disclosed for use in connection with the delivery of therapeutic agents and other substances through the skin and other surfaces. The devices are typically pressed against the skin in an effort to pierce the stratum corneum such that the therapeutic agents and other substances can sequentially or simultaneously pass through that layer and into the tissues below. Microneedles of these devices pierce the stratum corneum upon contact, making a plurality of microscopic slits which serve as passageways through which molecules of active components can be delivered into the body. In delivering an active component, the microneedle device can be provided with a reservoir for temporarily retaining an active component in liquid form prior to delivering the active component through the stratum corneum. In some constructions, the microneedles can be hollow to provide a liquid flow path directly from the reservoir and through the microneedles to enable delivery of the therapeutic substance through the skin. In alternate constructions, active component(s) may be coated on the microneedle array and delivered directly through the skin after the stratum corneum has been punctured.

Microneedle arrays can be used in conjunction with an injection and infusion apparatus (i.e., an "applicator" that applies the hollow microneedles to the skin and facilitates infusion of a substance through the hollow microneedles) capable of being used several times or as a single-use device. The microneedle arrays are generally used once and then discarded.

SUMMARY

It has now been found that an interaction between an article comprising a plurality of hollow microneedles and a skin surface against which the article is urged can result in undesirable effects on the penetration of at least one microneedle of the plurality into the skin. It has further been found that, when the article comprises an array of microneedles, one of the effects can be significant variability in the depth of penetration into the skin by one or more of the microneedles in the array. The present inventors recognized the consistency of penetration depth can be controlled by including several features into the design of the article. The inventive design features result in the ability to rapidly, effectively and consistently insert the needles to a desired depth in the skin and quickly deliver a pharmaceutically-effective dose in a variety of skin locations. In addition, certain features of the inventive design permit simpler, more robust processes to be used for the manufacture of the articles.

The present disclosure generally relates to articles comprising microneedles and their use to deliver materials through the surface of skin or remove biological fluids through the surface of skin. In particular, the present disclosure relates to an article comprising an array of a plurality of microneedles that is configured to provide consistent depths of penetration for each microneedle of the plurality of microneedles by facilitating the contact between microneedles and skin and by reducing the possibility of contact between skin and non-microneedle surfaces during the use of the articles.

Some aspects of the present disclosure provide an article. The article can comprise a first side, a second side opposite the first side, and at least three hollow microneedles. The first side can comprise a central cavity portion and a platform portion that projects from the first side and that is not coplanar with the central cavity portion. The microneedles can extend from the platform portion in a first direction. The platform portion can substantially surround the central cavity portion and can comprise an inner perimeter proximate the central cavity portion and an outer perimeter distal the central cavity portion. Each of the at least three microneedles comprises a body that comprises an outer surface; a base segment having a base and a first shape that is defined by a first section of the outer surface; a tip segment having a tip and a second shape that is defined by a second section of the outer surface, wherein the second shape is distinct from the first shape; a transition plane that delineates the base segment and the tip segment; and a central axis. A first angle, defined by the central axis of each of the at least three microneedles and a shortest line extending from the outer perimeter of the platform and through the transition plane of the at least one microneedle, is greater than 50° and less than or equal to about 85°. In any embodiment, the first angle can be about 65° to about 75°, inclusive. In any of the above embodiments, the first angle can be about 70°.

Other aspects of the present disclosure provide an article. The article can comprise a first side, a second side opposite the first side, and at least three hollow microneedles. The first side can comprise a central cavity portion and a platform portion that projects from the first side and that is not coplanar with the central cavity portion. The microneedles can extend from the platform portion in a first direction. The platform portion can substantially surround the central cavity portion and can comprise an inner perimeter proximate the central cavity portion and an outer perimeter distal the central cavity portion. Each of the at least three microneedles comprises a body that comprises an outer surface; a base segment having a base and a first shape that is defined by a first section of the outer surface; a tip segment having a tip and a second shape that is defined by a second section of the outer surface, wherein the second shape is distinct from the first shape; a transition plane that delineates the base segment and the tip segment; and a central axis. Each of the at least three microneedles comprises a height measured from the base to the tip. The tip segment of each of the at least three microneedles can define at least about 45% of the height of the microneedle. In any embodiment, the tip segment of each of the at least three microneedles can define at least about 70-80% of the height of the microneedle.

The phrase "injection apparatus" refers to an integrated device capable of delivering or extracting a fluid over a certain period and is not limited to devices intended solely for an infusion. Accordingly, an injection apparatus may be used, for example, for injecting fluid into the dermis or extracting fluid from tissue.

The term "transdermally" and variations thereof, is generally used to refer to any type of delivery of an active ingredient that crosses any portion of skin. That is, transdermally can generally include systemic delivery (i.e., where the active ingredient is transported across, or substantially through, the dermis such that the active ingredient is delivered into the bloodstream), as well as intradermal delivery (i.e., where the active ingredient is transported partially through the dermis, e.g., across the outer layer (stratum corneum) of the skin, where the active ingredient is delivered into the skin, e.g., for treating psoriasis or for local anesthetic delivery). That is, transdermal delivery as used herein includes delivery of an active ingredient that is transported across at least a portion of skin (but not necessarily all of the layers of skin), rather than merely being topically applied to an outer layer of the skin.

The phrase "hollow microneedle" refers to a specific microscopic structure that is designed for piercing the stratum corneum to facilitate the delivery of drugs through the skin. By way of example, microneedles can include needle or needle-like structures, as well as other structures capable of piercing the stratum corneum and delivering liquid drug formulations to skin or tissue layers beneath the stratum corneum.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

As used herein, "a," "an," "the," "at least one," and "one or more" are used interchangeably. Thus, for example, a microneedle can be interpreted to mean "one or more" microneedles.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the accompanying drawings and the description below. Other features, objects and advantages will become apparent from the description and drawings, and from the claims.

BRIEF DESCRIPTION OF DRAWINGS

The present invention will be further explained with reference to the drawing figures listed below, where like structure is referenced by like numerals throughout the several views.

DETAILED DESCRIPTION

Figure 1:
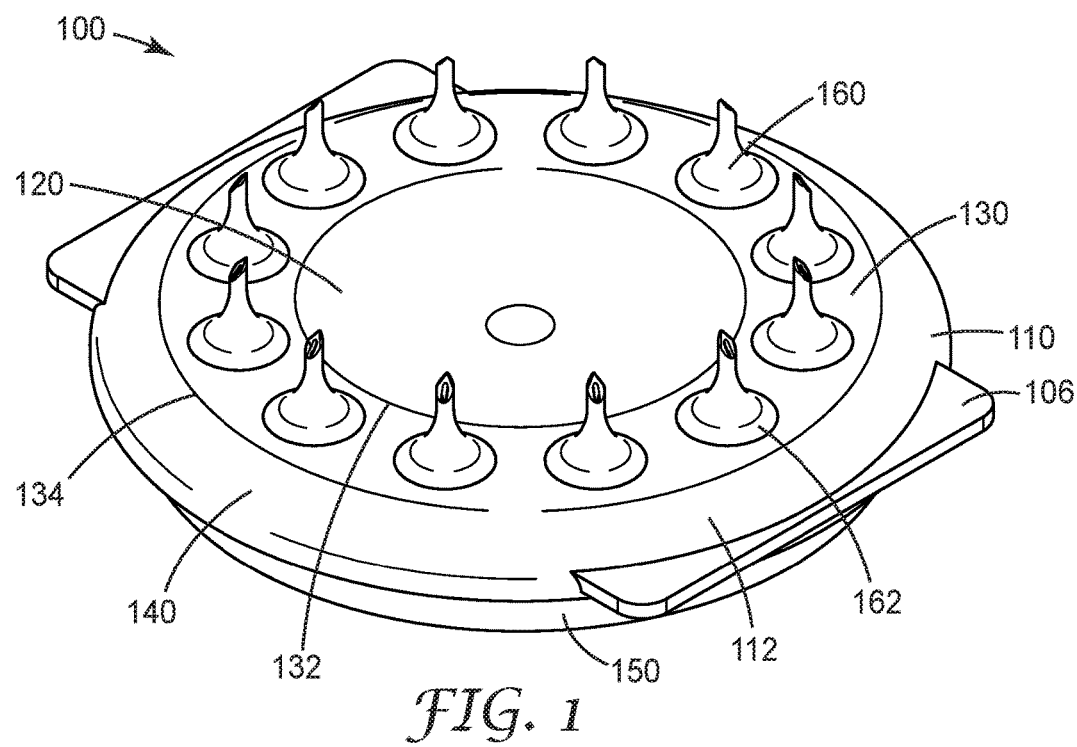
FIG. 1 is a perspective view showing one embodiment of an article comprising a plurality of microneedles according to the present disclosure.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. It is to be understood that other embodiments may be utilized, and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to articles comprising microneedles and their use to deliver materials through the surface of skin or remove biological fluids through the surface of skin. In particular, the present disclosure relates to an article comprising an array of a plurality of microneedles that is configured to provide consistent depths of penetration for each microneedle of the plurality of microneedles by facilitating the contact between microneedles and skin and by reducing the possibility of contact between skin and non-microneedle surfaces during the use of the articles.

Turning to the drawings, FIGS. 1-4 show various views of one embodiment of an article 100 according to the present disclosure. The article 100 comprises a first side 112 and a second side 114 opposite the first side 112. The first side 112 comprises a central cavity portion 120 and a platform portion 130. The platform portion 130 projects from the first side 112 and is not coplanar with the central cavity portion 120. In the illustrated embodiment of FIGS. 1-4, the central cavity portion 120 and platform portion 130 are both formed as portions of a unitary body 110. However, in any embodiment, it is contemplated that the central cavity portion 120 and platform portion 130 may be separate parts (not shown) that are disposed adjacent each other in the article.

The central cavity portion 120 is not coplanar with the platform portion 130. Although the illustrated embodiment of FIGS. 1-4 depict the central cavity portion 120 having a curvilinear surface that slopes away from the plane formed by the platform portion 130, it is contemplated that, in any embodiment, the central cavity portion may comprise one or more angular surfaces (not shown) that are not coplanar with the platform portion.

In any embodiment, the central cavity portion 120 may consist of a solid structure, as shown in FIGS. 1-4. Alternatively, in any embodiment, the central cavity portion may comprise, consist essentially of, or consist of an opening (e.g., a through-hole, not shown).

The platform portion 130 substantially surrounds the central cavity portion 120. The platform portion 130 comprises an inner perimeter 132 proximate the central cavity portion 120 and an outer perimeter 134 distal the central cavity portion. In any embodiment, the inner perimeter 132 and/or outer perimeter 134 comprise a substantially rounded edge, as shown in the side view of the outer perimeter in FIG. 2 and as shown in the cross-sectional view of both perimeters of FIG. 4. Alternatively, in any embodiment, the inner perimeter 132 and/or outer perimeter 134 comprise a substantially angular edge (not shown).

Figure 2:
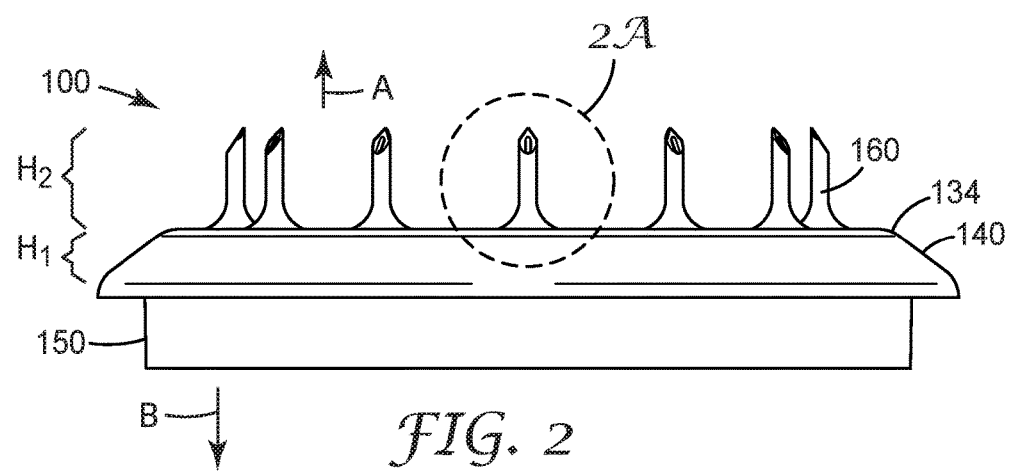
FIG. 2 is a side view of the article of FIG. 1.
Figure 3:
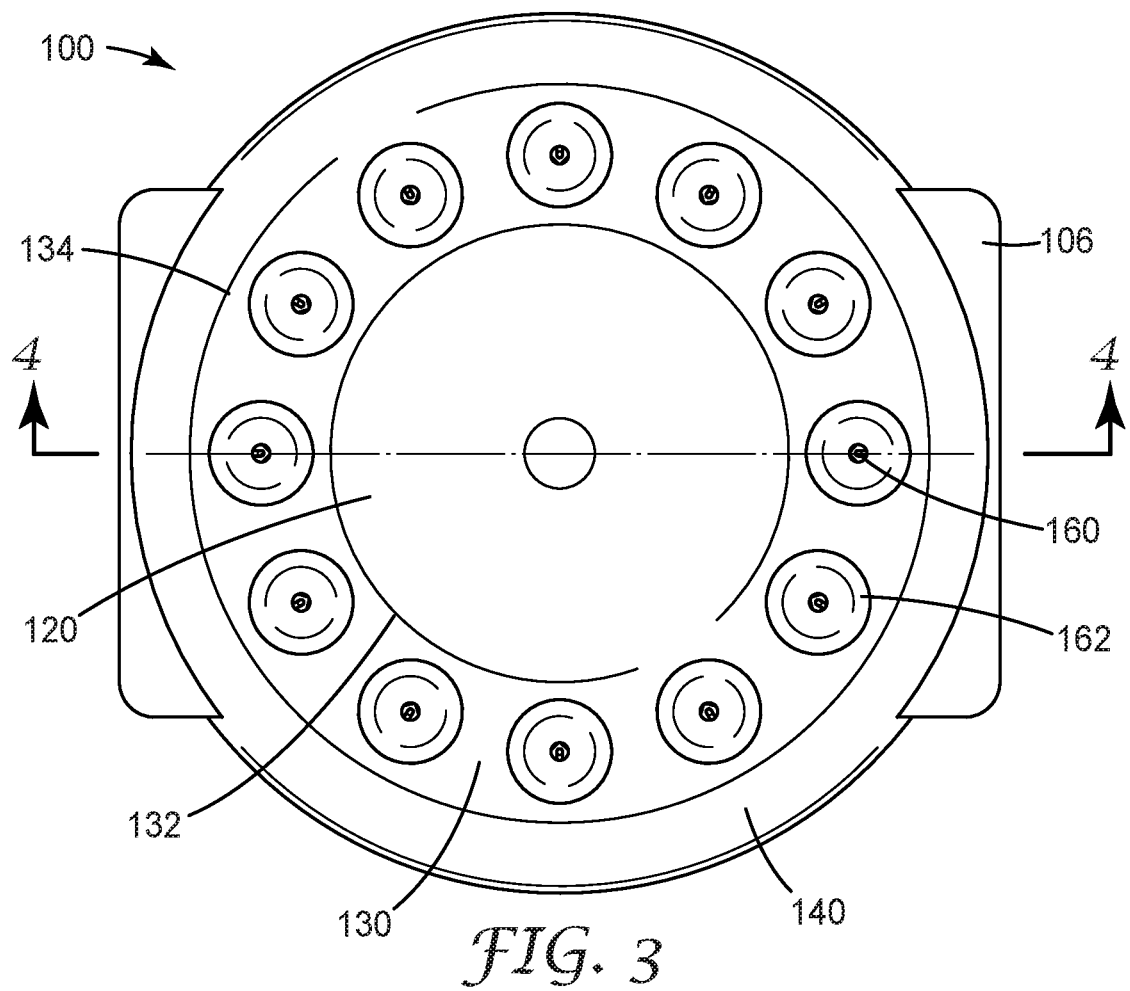
FIG. 3 is a plan view of the first side of the article of FIG. 1.

The article 100 further comprises a plurality of hollow microneedles 160 extending from the platform portion 130 in a first direction (see arrow "A", FIG. 2). In any embodiment, the plurality of hollow microneedles 160 can comprise an array. The array can comprise a circular arrangement (i.e., a circulate array), as shown in FIG. 3. It is contemplated that other arrays, having other rectilinear or curvilinear geometric shapes (e.g., a square, a rectangle, an oval, a hexagon; not shown) are also useful in an article according to the present disclosure.

Figure 2A:
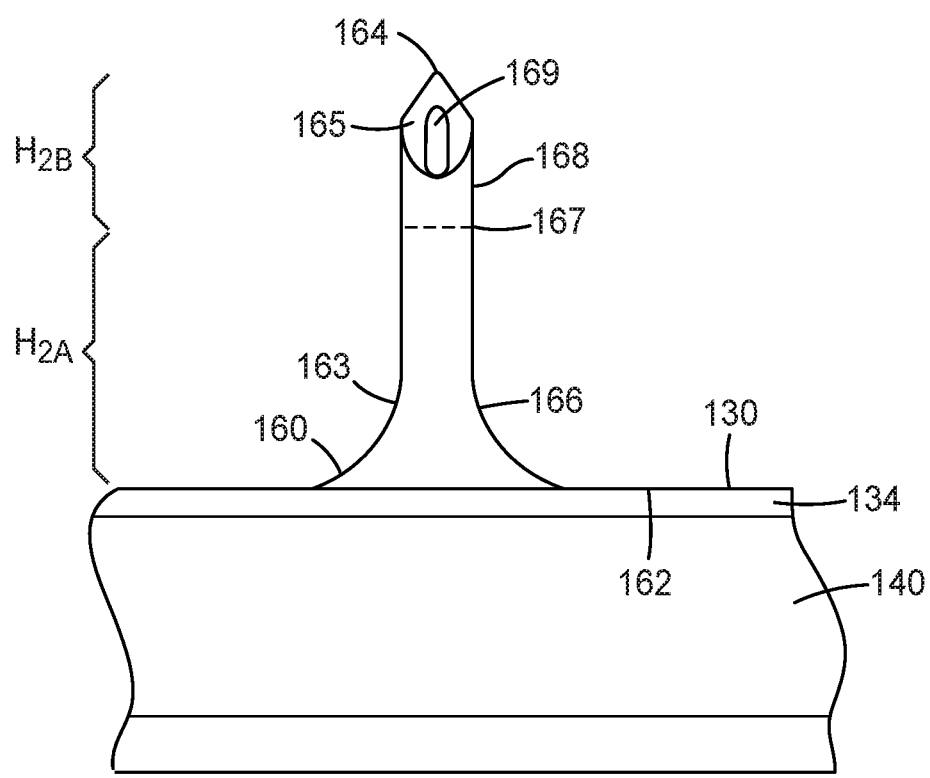
FIG. 2A is a detail view of a portion of the article of FIG. 2.

FIG. 2A shows a detail view of one of the microneedles 160 of the article 100 of FIG. 2. In any embodiment of the article 100, each microneedle 160 of the plurality comprises a body that comprises an outer surface 163, a base segment 166, and a tip segment 168. The base segment 166 comprises a base 162 where the microneedle 160 extends from the platform portion 130. The base segment 166 has a first shape that is defined by the outer surface 163 of the base segment. In the illustrated embodiment of FIG. 2A, the first shape is crateriform (i.e., a generally-conical shape with a radius of curvature) and, thus, the diameter of the microneedle is wider at the base 162 than at the tip. Optionally, the base segment 166 has a concave outer surface.

The tip segment 168 comprises a tip 164. The tip 164 is the part of the microneedle 160 that is furthest away from the base 162. The tip segment 168 has a second shape that is defined by the outer surface 163 of the microneedle 160. The second shape is distinguishable from the first shape. The respective shapes of the base segment 166 and the tip segment 168 become distinguishable at a transition plane 167. "Transition plane", as used herein is the plane where an angle formed by a tangent of the outer surface 163 of the microneedle and the central axis changes from a first (tip-proximal) angle of ≤10° to a second (tip-distal) angle of greater than about 10°. In the illustrated embodiment of FIG. 3A, the outer surface 163 of the microneedle 160 is substantially parallel to the central axis (not shown). However, at the transition plane 167, the substantially straight outer surface of the tip segment 168 (i.e. second shape) changes to a flared radius of curvature of the base segment 166 (i.e. first shape) and the angle formed by the intersection of a tangent (not shown) of the outer surface and the central axis (not shown) becomes greater than about 10°. The substantially cylindrically-shaped tip segment 168 of FIG. 2A is truncated by a bevel 165 that forms a tip 164 that is sharp enough to pierce stratum corneum.

Figure 4:
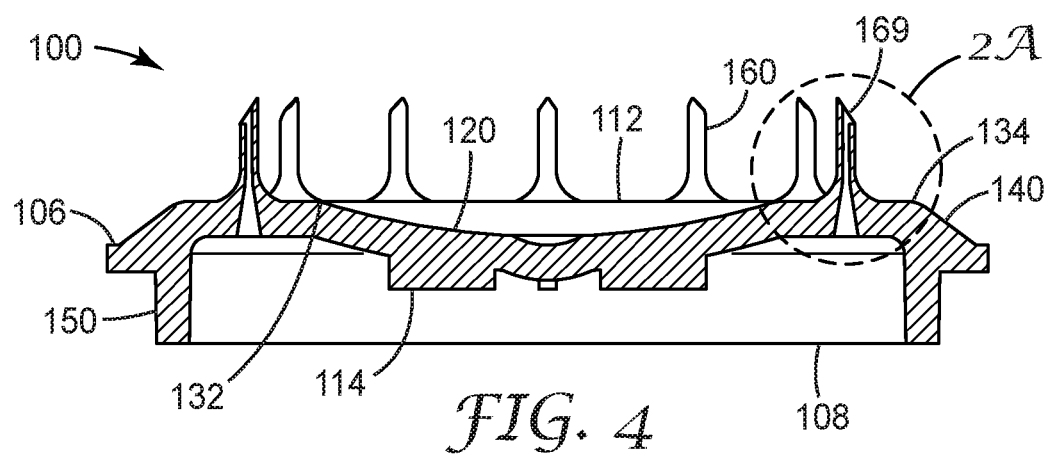
FIG. 4 is a cross-sectional view, taken along line 4-4, of the article of FIG. 3.

Each microneedle 160 of the plurality further comprises a hollow channel 169. The hollow channel 169 optionally extends all the way through the article from the first side 112 through the second side 114, as shown in FIG. 4. In any embodiment, the hollow channel can provide a dead-end reservoir (e.g., a dead-end reservoir in the body of the microneedle, not shown) in which to load an active ingredient for injection/delivery into the skin, for example. In any embodiment, a hollow channel 169 extending through the article 100 can be fluidically connected to a reservoir 108 disposed on the second side of the article and an active ingredient can be infused into a patient from the reservoir 108 of the article 100 and through the hollow channel 169 of the microneedle 160.

In any embodiment, the first side 112 optionally comprises a microneedle-free peripheral portion 140 extending laterally from at least a part of the outer perimeter 134 of the platform portion 130. In any embodiment, the peripheral portion 140 substantially surrounds the platform portion 130. The peripheral portion 140 is canted away from the platform portion 130 in a second direction (see arrow "B", FIG. 2) opposite the first direction. In the illustrated embodiment of FIGS. 1-4, the central cavity portion 120, the platform portion 130, and the peripheral portion 140 are all formed as portions of a unitary body 110. However, in any embodiment, it is contemplated that the peripheral portion 140 and platform portion 130 may be separate parts (not shown) that are disposed adjacent each other in the article.

Figure 4A:
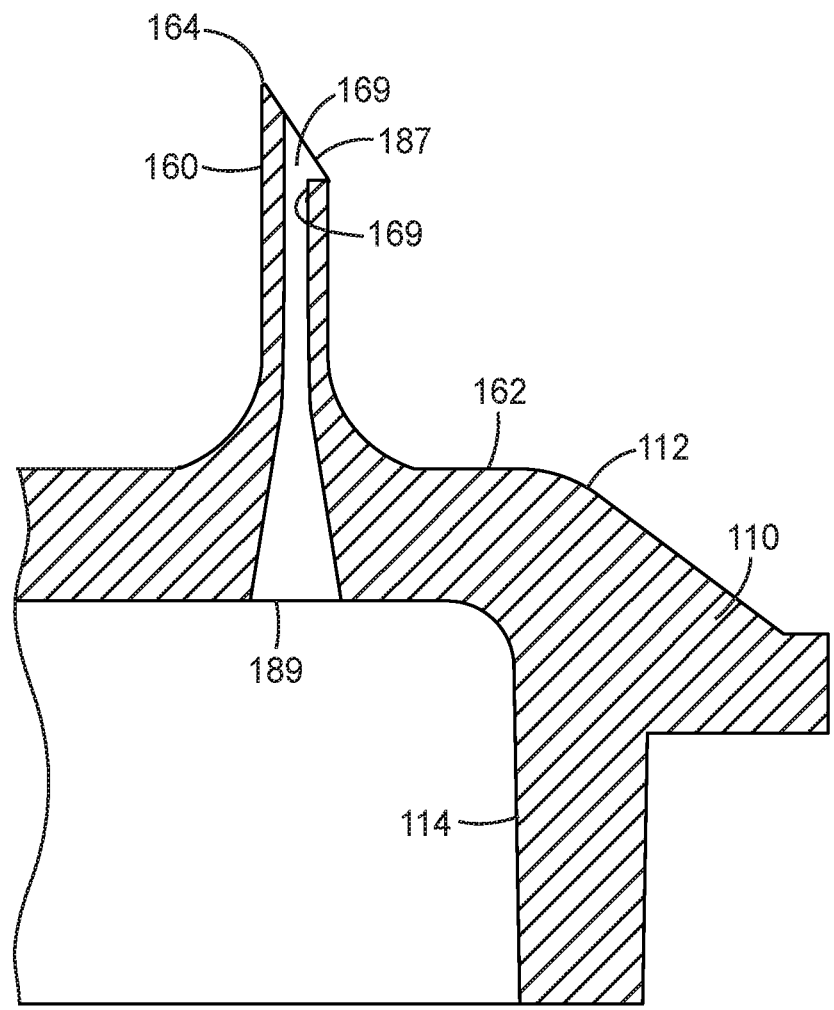
FIG. 4A is a detailed cross-sectional view of one of the hollow microneedles of FIG. 4.

FIG. 4A shows a detail view of one of the sectioned microneedles 160 disposed on the first side 112 of the article the unitary body 110 of FIG. 4. The microneedle 160 comprises a first opening 187 that opens proximate the tip 164 into a hollow channel 169 that extends all the way through the body 110 to a second opening 189 on the second side 112 of the body 110.

Optionally, in any embodiment, the article 100 further may comprise a tab (e.g., tab 106). The tab 106 may be useful for manufacturing purposes or for alignment purposes during use. In the illustrated embodiment, the tab 106 extends laterally from the peripheral portion 140; however other useful configurations will be apparent to a person having ordinary skill in the art.

Optionally, the article 100 further comprises a sidewall 150 extending substantially in the direction (i.e., second direction "B" shown in FIG. 2) opposite the plurality of microneedles 160. The side wall 150 of the illustrated embodiment forms a reservoir 108 on the second side 114 of the article 100. The reservoir 108 optionally can be sealed (not shown) and can contain an active agent (e.g., a drug) to be delivered by injection via the plurality of microneedles 160.

Referring to FIG. 2, the article can comprise at least two height dimensions. The first height dimension $H_1$ is the height of the canted peripheral portion 140 extending in the second direction B from the platform portion 130. The second height dimension $H_2$ is the height of each microneedle 160 extending in the first direction A from the platform portion 130. Referring back to FIG. 2A, each microneedle 160 of the plurality comprises two height components (first height component $H_{2A}$ and second height component $H_{2B}$, respectively) that contribute to the total height of the microneedle 160. The first height component represents the height of the base segment 166 of the microneedle 160 and the second height component represents the height of the tip segment 168 of the microneedle.

In any embodiment, the first height component of each microneedle of the plurality according to the present disclosure is about 50 μm to less than 500 μm. Preferably, the first height component of each microneedle of the plurality according to the present disclosure is about 150 μm to about 350 μm. More preferably, the first height component of each microneedle of the plurality according to the present disclosure is about 200 μm to about 300 μm. Even more preferably, the first height component of each microneedle of the plurality according to the present disclosure is about 250 μm to about 270 μm.

In any embodiment, the second height component of each microneedle of the plurality according to the present disclosure is about 300 μm to about 1940 μm. In any embodiment, the second height component of each microneedle of the plurality according to the present disclosure is about 540 μm to about 1740 μm. When the first height component is about 250 μm to about 270 μm, preferably, the second height component of each microneedle of the plurality according to the present disclosure is about 540 μm to about 1240 μm. When the first height component is about 250 μm to about 270 μm, more preferably, the second height component of each microneedle of the plurality according to the present disclosure is about 640 μm to about 840 μm. When the first height component is about 250 μm to about 270 μm, even more preferably, the second height component of each microneedle of the plurality according to the present disclosure is about 700 μm to about 800 μm.

In order to get consistent and effective delivery of an active compound to the proper location in the skin, the inventors have found that the configuration of an article comprising at least three microneedles according to the present disclosure should facilitate penetration of all of the at least three microneedles until at least the tip portion of each microneedle is fully inserted into the skin.

In one aspect, in any embodiment, there may exist a predefined proportional relationship between first height component and the second height component of each microneedle of the plurality in an article according to the present disclosure. In any embodiment, the tip segment (as measured from the transition plane to the tip of at least one microneedle of the plurality of microneedles) defines at least about 45% of the height of the at least one microneedle. In any embodiment, the tip segment (as measured from the transition plane to the tip of each microneedle of the plurality of microneedles) defines at least about 45% of the height of the microneedles. In any embodiment, the tip segment (as measured from the transition plane to the tip of at least one microneedle of the plurality of microneedles) defines about 50-95% of the height of the at least one microneedle. In any embodiment, the tip segment (as measured from the transition plane to the tip of each microneedle of the plurality of microneedles) defines about 50-95% of the height of the microneedles. In any embodiment, the tip segment (as measured from the transition plane to the tip of at least one microneedle of the plurality of microneedles) defines about 60-85% of the height of the at least one microneedle. In any embodiment, the tip segment (as measured from the transition plane to the tip of each microneedle of the plurality of microneedles) defines about 60-85% of the height of the microneedles. In any embodiment, the tip segment (as measured from the transition plane to the tip of at least one microneedle of the plurality of microneedles) defines up to about 70-80% (inclusive) of the height of the at least one microneedle. In any embodiment, the tip segment (as measured from the transition plane to the tip of each microneedle of the plurality of microneedles) defines up to about 70-80% (inclusive) of the height of the microneedles.

Figure 5A:
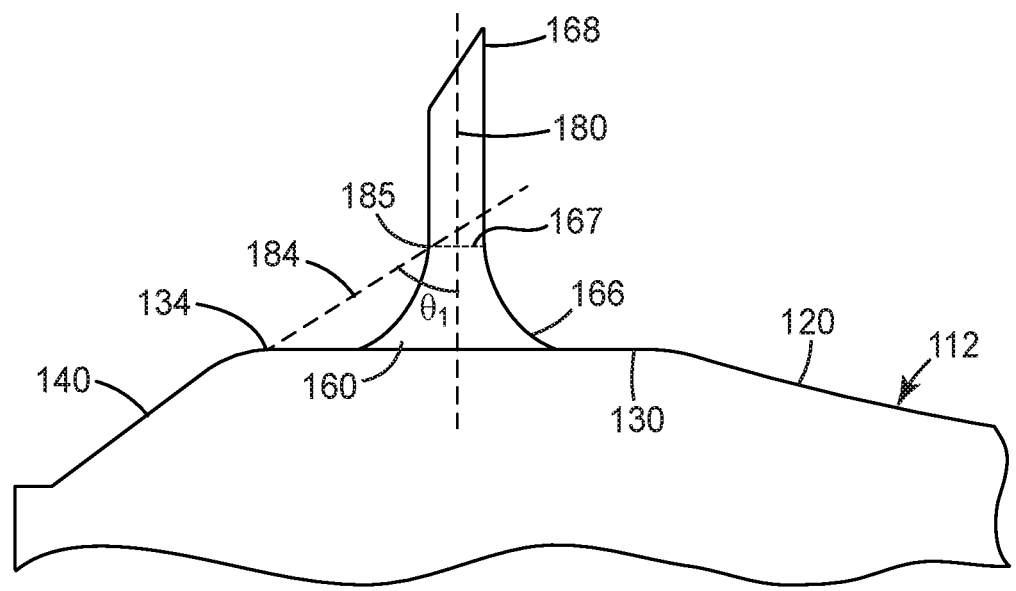
FIG. 5A is a schematic side view, partially in section, of a portion of the article of FIG. 1, showing an angle $\theta_1$ formed by the intersection of a central axis of a microneedle with a line passing through a transition plane in the microneedle.
Figure 5B:
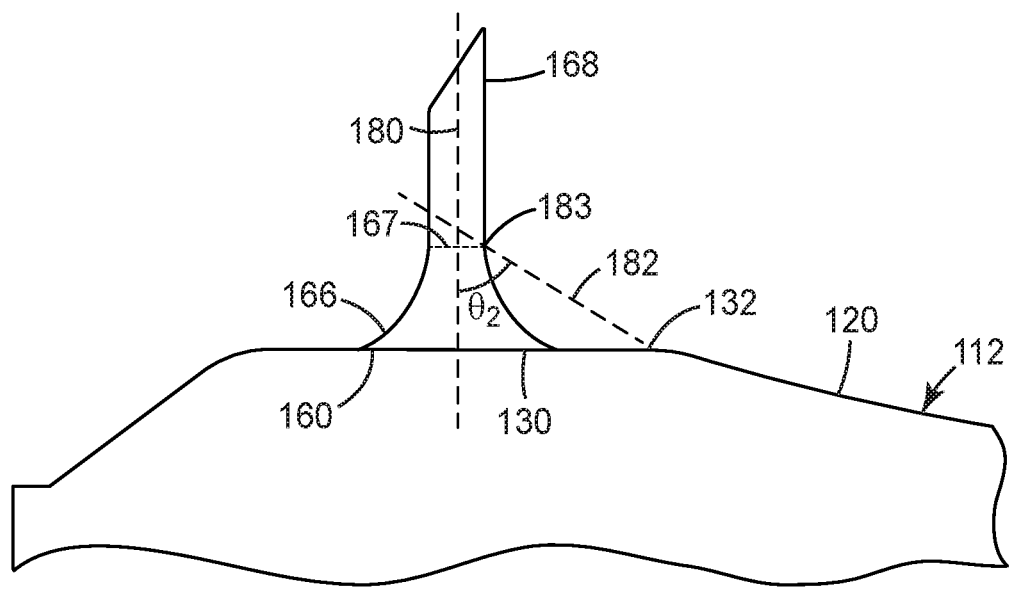
FIG. 5B is a schematic side view, partially in section, of the article of FIG. 5A, showing an angle $\theta_2$ formed by the intersection of a central axis of a microneedle with a line passing through a transition plane in the microneedle.
Figure 6:
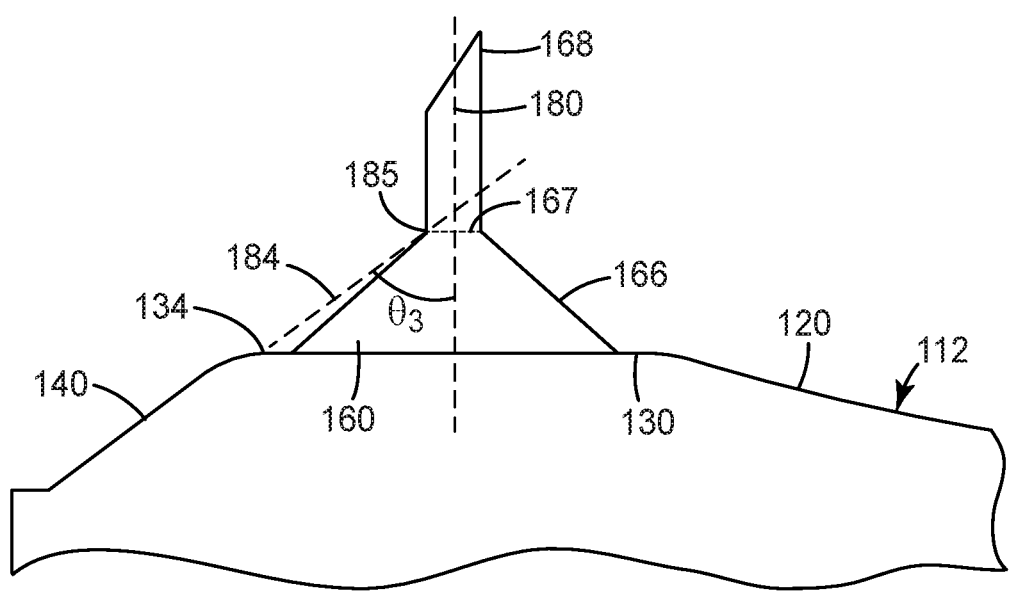
FIG. 6 is a schematic side view, partially in section, of a portion of another embodiment of an article comprising a microneedle, showing an angle 83 formed by the intersection of a central axis of a microneedle with a line passing through a transition plane in the microneedle.

In any embodiment, each microneedle 160 of the plurality of microneedles in an article of the present disclosure comprises a central axis 180 as shown in FIGS. 5A, 5B, and 6. The central axis 180 also represents a longitudinal axis of the microneedle 160 extending through the microneedle from the base 162 toward the tip 164. In one aspect, each microneedle 160 of the plurality may have a spatial relationship between a structural feature (i.e., the microneedle transition plane 167) of the microneedle 160 and one or more of the perimeters (i.e., inner perimeter 132 and outer perimeter 134) of the platform portion 130, as illustrated in FIGS. 5A-B.

In another aspect, in any embodiment, there may exist a spatial relationship between each microneedle of the plurality and the outer perimeter of the platform on which the microneedle projects in an article according to the present disclosure. FIG. 5A shows a schematic view of a section of an article comprising a plurality of microneedles according to the present disclosure. The article comprises a first side 112 having a central cavity portion 120, a platform portion 130, a canted peripheral portion 140, and an outer perimeter 134 disposed between the platform portion 130 and the peripheral portion 140, as described above. Extending from the platform portion 130 is a microneedle 160. The microneedle 160 comprises a base segment 166 with a first shape and a tip segment 168 with a second shape, the segments being separated by a transition plane 167. Also shown in FIG. 5A is the central axis 180 of the microneedle 160 and a shortest line 184 extending from the outer perimeter 134, through the closest point 185 of the transition plane 167 to the outer perimeter 134, to the central axis 180. The intersection of the shortest line 184 with the central axis 180 forms an angle $\theta_1$. In any embodiment of the article of the present disclosure the angle $\theta_1$ is greater than 50° to about 85°. In any embodiment, the angle $\theta_1$ is about 65° to about 75°. In any embodiment, the angle $\theta_1$ is less than about 68° to about 72°. In any embodiment, the angle $\theta_1$ is about 70°. A person having ordinary skill in the art will appreciate that, as the angle $\theta_1$ decreases, the amount of potential area of platform portion between the microneedle and the outer perimeter also decreases. The significance of this relationship is discussed below.

Alternatively, or additionally, there may exist a spatial relationship between the each microneedle of the plurality and the inner perimeter of the platform on which the microneedle projects. FIG. 5B shows a similar schematic view of the section of the article shown in FIG. 5A. The article comprises a first side 112 having a central cavity portion 120, a platform portion 130, a canted peripheral portion 140, and an inner perimeter 132 disposed between the platform portion 130 and the peripheral portion 140, as described above. Extending from the platform portion 130 is a microneedle 160. The microneedle 160 comprises a base segment 166 with a first shape and a tip segment 168 with a second shape, the segments being separated by a transition plane 167. Also shown in FIG. 5B is the central axis 180 of the microneedle 160 and a first shortest line 182 extending from the inner perimeter 132, through the closest point 183 of the transition plane 167 to the inner perimeter 132, to the central axis 180. The intersection of the first shortest line 182 with the central axis 180 forms an angle $\theta_2$. In any embodiment of the article of the present disclosure the angle $\theta_2$ is greater than 50° to about 85°. In any embodiment, the angle $\theta_2$ is about 65° to about 75°. In any embodiment, the angle $\theta_2$ is about 68° to about 72°. In any embodiment, the angle $\theta_2$ is about 70°. A person having ordinary skill in the art will appreciate that, as the angle $\theta_2$ decreases, the amount of potential area of platform portion between the microneedle and the inner perimeter also decreases. The significance of this relationship is discussed below.

The spatial relationships discussed above may apply regardless of the first and second shapes defined by the base segment and the tip segment of each microneedle of the plurality. FIG. 6 shows a schematic view of a section of an article comprising a plurality of microneedles similar to that shown in FIG. 5A expect the base segment 166 has a first shape that defines a truncated pyramid or truncated cone shape, rather than a crateriform shape. The article comprises a first side 112 having a central cavity portion 120, a platform portion 130, a canted peripheral portion 140, and an outer perimeter 134 disposed between the platform portion 130 and the peripheral portion 140, as described above. Extending from the platform portion 130 is a microneedle 160. The microneedle 160 comprises a base segment 166 with a first shape and a tip segment 168 with a second shape, the segments being separated by a transition plane 167. Also shown in FIG. 6 is the central axis 180 of the microneedle 160 and a second shortest line 184 extending from the outer perimeter 134, through the closest point 185 of the transition plane 167 to the outer perimeter 134, to the central axis 180. The intersection of the second shortest line 184 with the central axis 180 forms an angle $\theta_3$. In any embodiment of the article of the present disclosure the angle $\theta_3$ is greater than 50° to about 85°. In any embodiment, the angle $\theta_3$ is about 65° to about 75°. In any embodiment, the angle $\theta_3$ is about 68° to about 72°. In any embodiment, the angle $\theta_3$ is about 70°. A person having ordinary skill in the art will appreciate that, as the angle $\theta_3$ decreases, the amount of potential area of platform portion between the microneedle and the outer perimeter also decreases. The significance of this relationship is discussed below.

In any embodiment of an article according to the present disclosure, the transition plane of at least one microneedle of the plurality is disposed about 60 μm to about 490 μm away from the platform portion when measured along the central axis. In any embodiment of an article according to the present disclosure, the transition plane of at least one microneedle of the plurality is disposed about 200 μm to about 300 μm away from the platform portion when measured along the central axis. In any embodiment of an article according to the present disclosure, the transition plane of at least one microneedle of the plurality is disposed about 260 μm away from the platform portion when measured along the central axis.

In any embodiment of an article according to the present disclosure, the height of at least one microneedle (measured from the base to the tip) of the plurality is about 600 μm to about 2000 μm. In any embodiment of an article according to the present disclosure, the height of at least one microneedle (measured from the base to the tip) of the plurality is about 800 μm to about 1500 μm. In any embodiment of an article according to the present disclosure, the height of at least one microneedle (measured from the base to the tip) of the plurality is about 900 μm to about 1100 μm. In any embodiment of an article according to the present disclosure, the height of at least one microneedle (measured from the base to the tip) of the plurality is about 1000 μm.

In certain preferred embodiments, an article according to the present disclosure comprises a plurality of microneedles wherein the first height component of each microneedle is about 200 μm to about 300 μm, the second height component of each microneedle is about 640 μm to about 840 μm, the angle $\theta_1$ is about 65-75 degrees, and the angle $\theta_2$ is about 65-75 degrees. In these embodiments, the article comprises or is operatively coupled to a medicament reservoir and the article is part of an apparatus (e.g., an assembly) wherein the article is operatively coupled to at least one stored energy device that is capable of propelling the microneedles of the article at a velocity (before impact) of about 4 m/sec to about 12 m/sec and capable of urging fluid from the reservoir to and through the hollow microneedles. In any embodiment, a first stored energy component (e.g., a first spring) may be used to generate force to move the microneedles in a predefined direction (e.g., toward a skin impact site) from a first position (e.g., within a housing) to a second position (e.g., in contact with a skin surface) and a second stored energy component (e.g., a second spring) may be used to urge a fluid from the reservoir to (and through) the hollow microneedles.

In certain particularly-preferred embodiments, an article according to the present disclosure comprises a plurality of microneedles wherein the first height component of each microneedle is about 250 μm to about 270 μm, the second height component of each microneedle is about 700 μm to about 800 μm, the angle $\theta_1$ is about 68-72 degrees, and the angle $\theta_2$ is about 68-72 degrees. In these embodiment, the article comprises or is operatively coupled to a medicament reservoir and the article is part of an apparatus (e.g., an assembly) wherein the article is operatively coupled to a stored energy device (e.g., an injection and infusion applicator) that is capable of propelling the microneedles of the article at a velocity (before impact) of about 4 m/sec to about 12 m/sec or a velocity (before impact) of about 6 m/sec to about 9 m/sec. Advantageously, articles and assemblies of these preferred embodiments are capable of achieving highly-reproducible depths of penetration of each microneedle to a predefined depth (e.g., about 400 microns to about 800 microns) in skin tissue and delivery of highly-reproducible predefined volumes (e.g., about 0.2 mL to about 3 mL) of medicament within relatively short periods of time (e.g., about 1.5 minutes to about 4 minutes.

Arrays of microneedles according to the present disclosure comprise a plurality of spaced-apart microneedles extending from a plane (i.e., the platform portion 130, as shown in FIGS. 1-4). The configuration of the needles in the arrays (e.g., with respect to the edges of the article and with respect to nearest-neighbor microneedles) improve the penetration and, correspondingly, the delivery of medicament by each needle of the microarray.

Figure 7:
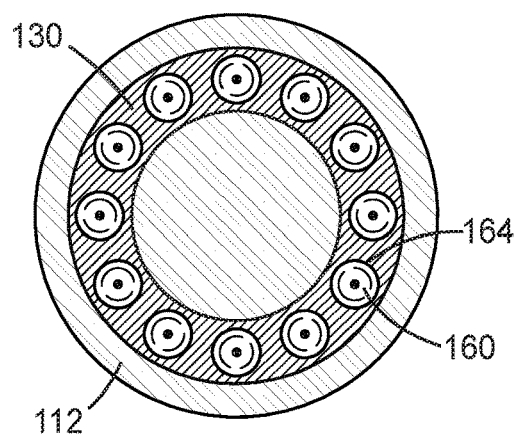
FIG. 7 is a plan view of an article according to the present disclosure; showing areas defined on the first side of the article.

In another aspect, in any embodiment, there may exist a spatial relationship between a first projected area defined by the first side of the article and a second area defined by the platform portion of the article according to the present disclosure. The term "projected area", as used herein, refers to an area of the article that is projected one side of the article and, thus, is capable of coming into contact with a surface (e.g., a skin surface) as that side of the article is urged toward the surface. FIG. 7 shows a top view (i.e., showing the first side 112) of an article 100 comprising a plurality of microneedles 160 according to the present disclosure. In the illustrated embodiment of FIG. 7, the article 100 comprises a plurality of microneedles 160 that form an array having a circular (circinate) shape. The first side 112 comprises a central cavity portion 120; a platform portion 130, from which the plurality of microneedles 160 extend, surrounding the central cavity portion; and a peripheral portion 140 surrounding the platform portion 130. The first side 112 defines a first area $A_1$ (i.e., a projected area) that includes the central cavity portion 120 and peripheral portion 140 (both shown with a first shading type), the area defined by the base of the microneedles 160 (not shaded), and the platform portion 130 (shown with a second shading type). The platform portion 130 defines a second area $A_2$ within the first area $A_1$. The second area includes the shaded platform area and the area defined by the base of the microneedles. In any embodiment, the second area $A_2$ is less than about 40% of the first area $A_1$. In any embodiment, the second area $A_2$ is less than about 35% of the first area $A_1$. In any embodiment, the second area $A_2$ is less than about 30% of the first area $A_1$. In any embodiment, the second area $A_2$ is about 25% to about 40% of the first area $A_1$.

In any embodiment, an article of the present disclosure can comprise a reservoir for holding a medicament. The reservoir can be in fluidic communication (or selective fluid communication) with each of the hollow microneedles.

In any embodiment, an article according to the present disclosure can be operatively coupled to other components (e.g., a reservoir, a stored energy component) described herein to form an injection and infusion apparatus. The injection and infusion apparatus can be used to deliver an injection of medicament into the skin of a subject. Such injection and infusion apparatuses are known in the art and include, for example, those described in International Patent Publication No. WO2014/193725, which is incorporated herein by reference in its entirety. The injection and infusion apparatuses can be actuated to use stored energy (e.g., from springs) to generate motive force that propels the microneedle array articles against skin at a predetermined velocity. In any embodiment, the injection and infusion apparatus can be configured to propel the microneedle array article at a velocity (before impact with skin) of about 2 m/sec to about 20 m/sec. In any embodiment, the injection and infusion apparatus can be configured to propel the microneedle array article at a velocity (before impact) of about 4 m/sec to about 12 m/sec. In any embodiment, the injection and infusion apparatus can be configured to propel the microneedle array article at a velocity (before impact) of about 6 m/sec to about 9 m/sec. In any embodiment, the injection and infusion apparatus can be configured to propel the microneedle array article at a velocity (before impact) of about 7 m/sec to about 8 m/sec.

In any embodiment, an apparatus comprising a microneedle article according to the present disclosure can be used in a method to insert the microneedles to a predefined depth in skin tissue. In any embodiment, the depth of penetration of each microneedle in the array can be about 400 μm to about 850 μm. In any embodiment, the average depth of penetration of each microneedle in the array can be about 580 μm to 750 μm.

In any embodiment, an apparatus comprising a microneedle article according to the present disclosure can be used in a method to deliver a predefined volume (e.g., about 0.2 mL to about 3 mL) of medicament into skin tissue within a predetermined amount of time. In any embodiment, the predetermined amount of time can be about 1.5 minutes to about 4 minutes. Advantageously, these delivery (i.e., infusion) times are relatively short. These infusion times can be achieved by delivering the medicament at a predetermined rate. The medicament infusion rates can be about 0.5 mL/minute to about 1.3 mL/minute.

Microneedle articles (e.g., including articles comprising hollow microneedles) that are made according to the present disclosure can have a variety of configurations and features, such as those described in the following patents and patent applications, the disclosures of which are incorporated herein by reference in their entirety. One embodiment for microneedle array articles includes the structures disclosed in U.S. Patent Application Publication No. 2005/0261631 (Clarke et al.), which describes microneedles having a truncated tapered shape and a controlled aspect ratio. Another embodiment for the microneedle articles includes the structures disclosed in U.S. Pat. No. 6,091,975 (Daddona et al.), which describes blade-like microprotrusions for piercing the skin. Still another embodiment for the microneedle articles includes the structures disclosed in U.S. Pat. No. 6,312,612 (Sherman et al.), which describes tapered structures having a hollow central channel. Yet still another embodiment for the microneedle array articles includes the structures disclosed in U.S. Pat. No. 6,379,324 (Gartstein et al.), which describes hollow microneedles having at least one longitudinal blade at the top surface of the tip of the microneedle. A further embodiment for the microneedle array articles includes the structures disclosed in U.S. Patent Application Publication Nos. US2012/0123387 (Gonzalez et al.) and US2011/0213335 (Burton et al.), which both describe hollow microneedles. A still further embodiment for the microneedle array articles includes the structures disclosed in U.S. Pat. No. 6,558,361 (Yeshurun) and U.S. Pat. No. 7,648,484 (Yeshurun et al.), which both describe hollow microneedle arrays and methods of manufacturing thereof.

Various embodiments of features of microneedles that can be employed in the microneedle articles of the present disclosure are described in PCT Publication No. WO2012/

074576 (Duan et al.), which describes liquid crystalline polymer (LCP) microneedles; and PCT Publication No. WO2012/122162 (Zhang et al.), which describes a variety of different types and compositions of microneedles that can be employed in the microneedles of the present disclosure.

Articles comprising microneedles having features according to the present disclosure can be made, for example, by injection molding processes that are known in the art. In some embodiments, the microneedle material can be (or include) a metal or a polymeric material, preferably a medical grade polymeric material. Exemplary types of medical grade polymeric materials include polycarbonate, liquid crystalline polymer (LCP), polyether ether ketone (PEEK), cyclic olefin copolymer (COC), polybutylene terephthalate (PBT). Preferred types of medical grade polymeric materials include polycarbonate and LCP.

The microneedle articles of the present disclosure can be manufactured in any suitable way such as by injection molding, compression molding, metal injection molding, stamping, or extrusion. In any embodiment, hollow microneedle arrays can be made by injection molding of a polymer such as medical grade polycarbonate or LCP, followed by laser drilling to form the channels of the microneedles. Nonlimiting examples of molding processes for molding polymeric materials into the solid microneedle articles of the present disclosure can be found in U.S. Pat. No. 8,088,321 (Ferguson et al.) and U.S. Patent Application Publication Nos. 2012/0258284 (Rendon) and 2012/0041337 (Ferguson et al.), each of which is incorporated herein by reference in its entirety. A non-limiting example of a publication that discloses the formation of articles comprising hollow microneedles is PCT Publication No. WO2014/105458, which is incorporated herein by reference in its entirety In some embodiments, the microneedle material can be (or include) a biodegradable polymeric material, preferably a medical grade biodegradable polymeric material. Exemplary types of medical grade biodegradable materials include polylactic acid (PLA), polyglycolic acid (PGA), PGA and PLA copolymer, polyester-amide polymer (PEA).

In some embodiments, the microneedles can be a prepared from a dissolvable, degradable, or disintegrable material referred to herein as "dissolvable microneedles". A dissolvable, degradable, or disintegrable material is any solid material that dissolves, degrades, or disintegrates during use. In particular, a "dissolvable microneedle" dissolves, degrades, or disintegrates sufficiently in the tissue underlying the stratum corneum to allow a therapeutic agent to be released into the tissue. The therapeutic agent may be coated on or incorporated into a dissolvable microneedle. In some embodiments, the dissolvable material is selected from a carbohydrate or a sugar. In some embodiments, the dissolvable material is polyvinyl pyrrolidone (PVP). In some embodiments, the dissolvable material is selected from the group consisting of hyaluronic acid, carboxymethylcellulose, hydroxypropylmethylcellulose, methylcellulose, polyvinyl alcohol, sucrose, glucose, dextran, trehalose, maltodextrin, and a combination thereof.

In any embodiment, the microneedles can be made from (or include) a combination of two or more of any of the above mentioned materials. For example, the tip of a microneedle may be a dissolvable material, while the remainder of the microneedle is a medical grade polymeric material.

A microneedle or the plurality of microneedles in a microneedle-containing article of the present disclosure can have a variety of shapes that are capable of piercing the stratum corneum. In some of the embodiments, one or more of the plurality of microneedles can have a segment (e.g., a base segment, a tip segment, or a combination thereof) having a square pyramidal shape, triangular pyramidal shape, stepped pyramidal shape, conical shape, microblade shape, or the shape of a hypodermic needle. In any embodiment, a segment (e.g., a base segment, a tip segment, or a combination thereof) of one or more of the plurality of microneedles can have a square pyramidal shape. In any embodiment, a segment (e.g., a base segment, a tip segment, or a combination thereof) of one or more of the plurality of microneedles can have a triangular pyramidal shape. In any embodiment, a segment (e.g., a base segment, a tip segment, or a combination thereof) of one or more of the plurality of microneedles can have a stepped pyramidal shape. In any embodiment, a segment (e.g., a base segment, a tip segment, or a combination thereof) of one or more of the plurality of microneedles can have a conical shape. In any embodiment, a segment (e.g., a base segment, a tip segment, or a combination thereof) of one or more of the plurality of microneedles can have a microblade shape. In any embodiment, a segment (e.g., a base segment, a tip segment, or a combination thereof) of one or more of the plurality of microneedles can have the shape of a hypodermic needle. In any embodiment, a microneedle array article may comprise an array of microneedles having a combination of any two or more of the foregoing microneedle shapes. The shape of any microneedle in the microneedle array article can be symmetric or asymmetric. The shape of any microneedle in the microneedle array article can be truncated (for example, the plurality of microneedles can have a truncated pyramid shape or truncated cone shape). In a preferred embodiment, each microneedle of the plurality of microneedles in a microneedle array article has a square pyramidal shape.

In any embodiment, each microneedle of the plurality of microneedles in a microneedle article is solid microneedles (that is, the microneedles do not comprise a through-hole). In any embodiment, each microneedle of the plurality of solid microneedles in a solid microneedle array article can have a segment (e.g., a base segment, a tip segment, or a combination thereof) with a square pyramidal shape, triangular pyramidal shape, stepped pyramidal shape, conical shape, or microblade shape. In a preferred embodiment, each microneedle of the plurality of solid microneedles in a solid microneedle array article has a segment (e.g., a base segment, a tip segment, or a combination thereof) with a square pyramidal shape or a conical shape with a radius of curvature.

In some embodiments, each microneedle of the plurality of microneedles in a microneedle array is a hollow microneedle (that is, the microneedle contains a hollow bore through the microneedle). The hollow bore can be from the base of the microneedle to the tip of the microneedle or the bore can be from the base of the microneedle to a position offset from the tip of the microneedle. In any embodiment, one or more of the plurality of hollow microneedles in a hollow microneedle array can have a conical shape, cylindrical shape, square pyramidal shape, triangular pyramidal shape, or the shape of a hypodermic needle.

In any embodiment, one or more microneedle of the plurality of hollow microneedles in a hollow microneedle array article can have a conical shape; optionally, with a radius of curvature. In any embodiment, one or more microneedle of the plurality of hollow microneedles in a hollow microneedle array article can have a cylindrical shape. In any embodiment, one or more microneedle of the plurality of hollow microneedles in a hollow microneedle array article can have a segment (e.g., a base segment, a tip segment, or a combination thereof) having a square pyramidal shape. In any embodiment, one or more microneedle of the plurality of hollow microneedles in a hollow microneedle array article can have a segment (e.g., a base segment, a tip segment, or a combination thereof) having a triangular pyramidal shape. In any embodiment, one or more microneedle of the plurality of hollow microneedles in a hollow microneedle array article can have a segment (e.g., a base segment, a tip segment, or a combination thereof) having the shape of a hypodermic needle. In a preferred embodiment, each microneedle of the plurality of hollow microneedles in a hollow microneedle array article has a segment (e.g., a base segment, a tip segment, or a combination thereof) with the shape of a conventional hypodermic needle.

In any embodiment, an article comprising a hollow microneedle according to the present disclosure may comprise a plurality of the microneedles. The plurality of the microneedles optionally may form an array. In any embodiment, the article can comprise an array of about 3 to about 30, inclusive, of the hollow microneedles of the present disclosure. In a preferred embodiment, the article can comprise an array of about 8 to about 20, inclusive, of the hollow microneedles of the present disclosure. In a more-preferred embodiment, the article can comprise an array of 12, 16, or 18 of the hollow microneedles of the present disclosure.

In any embodiment of an article comprising a plurality of hollow microneedles according to the present disclosure, the overall height of each microneedle is about 600 μm to about 2000 μm. In any embodiment of an article comprising a plurality of hollow microneedles according to the present disclosure, the overall height of each microneedle is about 700 μm to about 1500 μm. In any embodiment of an article comprising a plurality of hollow microneedles according to the present disclosure, the overall height of each microneedle is about 900 μm to about 1100 μm.

In any embodiment of an article comprising a plurality of hollow microneedles according to the present disclosure, a hollow channel extending through each of the microneedles has a diameter, proximate the tip of the microneedle, of about 10 μm to about 200 μm. In any embodiment of an article comprising a plurality of hollow microneedles according to the present disclosure, a hollow channel extending through each of the microneedles has a diameter, proximate the tip of the microneedle, of about 10 μm to about 120 μm. In any embodiment of an article comprising a plurality of hollow microneedles according to the present disclosure, a hollow channel extending through each of the microneedles has a diameter, proximate the tip of the microneedle, of about 25 μm to about 75 μm.

In any embodiment of an article comprising a plurality of hollow microneedles according to the present disclosure, a hollow channel extending through each of the microneedles has a cross-sectional area of about 75 $\mu m^2$ to about 32,000 $\mu m^2$. In any embodiment of an article comprising a plurality of hollow microneedles according to the present disclosure, a hollow channel extending through each of the microneedles has a cross-sectional area of about 75 $\mu m^2$ to about 18,000 $\mu m^2$. In any embodiment of an article comprising a plurality of hollow microneedles according to the present disclosure, a hollow channel extending through each of the microneedles has a cross-sectional area of about 700 $\mu m^2$ to about 3,000 $\mu m^2$.

The microneedle array articles of the present disclosure can be manufactured by injection molding of a polymer such as medical grade polycarbonate or LCP. Typically, these processes use molds to form the substrate with the microneedles extending therefrom.

In any embodiment, at least one hollow microneedle in an article according to the present disclosure can have a tip segment that has any shape or structure that facilitates, or does not interfere with, the ability of the microneedle to penetrate the surface of skin. In addition, the tip segment may comprise an opening (e.g., either a depression, dead-end cavity, or a through-hole that extends all the way through the microneedle) that facilitates the delivery of (and, optionally, storage therein) an active compound. In any embodiment, at least one hollow microneedle of the plurality of microneedles comprises a base, an elongated body having a central axis and a body diameter, and a tip segment with two bevel faces. The tip segment comprises a tip, a first bevel face oriented diagonally with respect to the central axis and extending through at least 75% of the body diameter, a second bevel face oriented substantially perpendicular to the central axis and intersecting the first bevel face, a bevel opening defined by a first edge of the first bevel face and a second edge of the second bevel face. A microneedle tip with two bevel faces is described in PCT Publication No. WO2015/009524 and incorporated herein by reference in its entirety.

In any embodiment, at least one hollow microneedle in an article according to the present disclosure can have a tip segment that comprises an opening that is formed by two channels that merge to form the opening. Thus, in these embodiments, the at least one microneedle comprises a base, an elongated body having a central axis, a tip segment with a beveled surface and a bevel opening in the bevel surface, a first channel that extends axially from the bevel opening through at least a portion of the elongated body, and a second channel that extends radially from the first channel to the bevel opening. The first channel has a first wall that is substantially aligned with the central axis. The second channel has a second wall that is oriented substantially orthogonal to the central axis. The first channel and second channel merge to form the bevel opening. A microneedle tip that comprises an opening that is formed by two channels that merge to form the opening, is described in PCT Publication No. WO2015/009523 and incorporated herein by reference in its entirety.

In any embodiment, articles of the present disclosure can be used with an injection and infusion apparatus (e.g., a single-use applicator or a reusable applicator) that is configured to urge the plurality of microneedles of the article against a skin surface. In any embodiment, actuation of the injection and infusion apparatus can occur through single actuation or through dual actuation. A non-limiting example of a single-actuation injection and infusion apparatus is disclosed in US Patent Application Publication No. 2012/0123387 (Gonzalez et al.), which is incorporated herein by reference in its entirety. The use of microneedle articles with a dual-actuation or dual automatic actuation is described, for example, in PCT Publication No. WO2014/099404, which is incorporated herein by reference in its entirety.

In any embodiment, an article of the present disclosure can be used with an injection and infusion apparatus comprising an adhesive assembly such as, for example, the injection and infusion apparatus comprising the adhesive assembly described in PCT Publication No. WO2014/099404. In any embodiment, the adhesive assembly can comprise a skin-contact adhesive layer such as, for example, the injection and infusion apparatus comprising the skin-contact adhesive layer described in PCT Publication No. WO2014/099404. In any embodiment, the skin-contact adhesive layer can comprise an annular configuration that, in use, surrounds the microneedle article of the present disclosure and, optionally, secures the article to a skin surface while an active compound (e.g., an active compound that is part of a pharmaceutical composition) is delivered from (or through) the microneedle into a patient.

Figure 8:
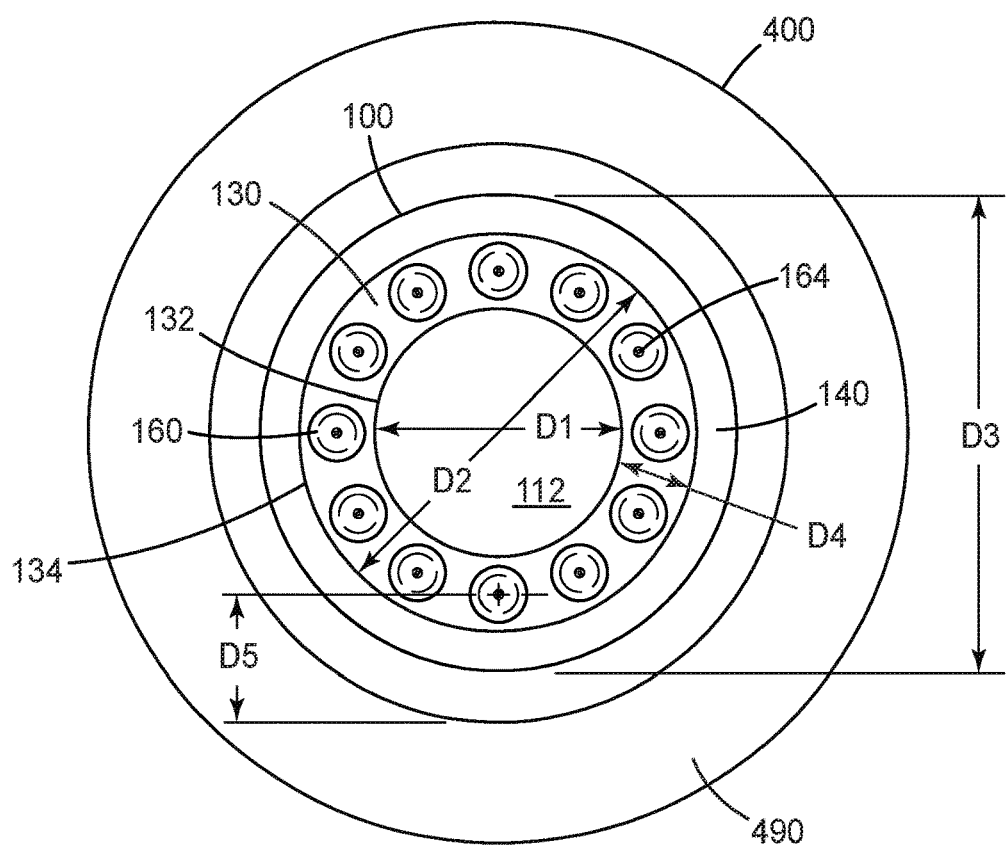
FIG. 8 is a plan view of a portion of an injection and infusion applicator coupled to an article comprising a plurality of microneedles according to the present disclosure; showing various dimensions associated with the article and the injection and infusion applicator.

FIG. 8 shows a plan view of a portion of the skin-facing surface of one embodiment of an injection and infusion apparatus configured for use with an article comprising a plurality of hollow microneedles according to the present disclosure. The injection and infusion apparatus 400 comprises a skin-contact adhesive layer 490 that substantially surrounds the article 100. The article comprises a first side 112 that comprises a central cavity portion 120 surrounded by a platform portion 130 that is not coplanar with the central cavity portion 120 (i.e., the platform is raised above the central cavity). A circinate array of spaced-apart microneedles 160 extend from the first side of the platform portion 130. The first side 112 further comprises an optional peripheral portion 140 that surrounds the platform portion 130 and that is not coplanar with the platform portion (i.e., the platform is raised above the peripheral portion). The article 100 is attached (e.g., detachably attached) to the injection and infusion apparatus 400 using various attachment means (e.g., an adhesive, a clamp, friction fit, and the like, not shown).

Also shown in FIG. 8 are various spatial dimensions associated with the article 100 and the injection and infusion apparatus. In the illustrated embodiment, the platform portion 130 is a ring-shaped (i.e., circinate) platform that surrounds the central cavity portion. Dimension D1 represents the diameter of the central cavity portion 120, as defined by the inner perimeter 132 of the platform portion 130. Dimension D2 represents the outer diameter of the platform portion 130, as defined by the outer perimeter 134 of the platform portion. Dimension D3 represents the outer diameter of the ring-shaped peripheral portion 140 that surrounds the platform portion 130. Dimension D4 represents the width of the platform portion, as measured along a radius (not shown) extending from the center of the circular-shaped article. In addition, D5 represents the shortest distance, as measured along a radius (not shown) extending from the center of the circular-shaped article, between the tip of a microneedle 160 and the skin-contact layer adhesive 490 of the injection and infusion apparatus 400. In a preferred embodiment, the shape of the skin-contact adhesive layer is shaped and dimensioned so that the shortest distance between each microneedle tip in the array is and the skin-contact adhesive layer 490 approximately equal (e.g., less than about 10% variability).

EXEMPLARY EMBODIMENTS

Embodiment A is an article, comprising:
a first side comprising a central cavity portion and a platform portion that projects from the first side and that is not coplanar with the central cavity portion;
a second side opposite the first side; and
at least three hollow microneedles extending from the platform portion in a first direction;
wherein the platform portion substantially surrounds the central cavity portion;
wherein the platform portion comprises an inner perimeter proximate the central cavity portion and an outer perimeter distal the central cavity portion;
wherein the at least three hollow microneedles each comprise a body that comprises:
an outer surface;
a base segment having a base and a first shape that is defined by a first section of the outer surface;
a tip segment having a tip and a second shape that is defined by a second section of the outer surface, wherein the second shape is distinct from the first shape;
a transition plane that delineates the base segment and the tip segment; and
a central axis;
wherein a first angle, defined by the central axis of each of the at least three hollow microneedles and a shortest line extending from the outer perimeter of the platform and through the transition plane of the microneedle, is greater than 50° and less than or equal to about 85°.

Embodiment B is the article of Embodiment A, wherein the first angle is about 65° to about 75°.

Embodiment C is the article of Embodiment B, wherein the first angle is about 68° to about 72°.

Embodiment D is the article of Embodiment C, wherein the first angle is about 70°.

Embodiment E is the article of any one of the preceding Embodiments, wherein a second angle, defined by the central axis and a shortest line extending from the inner perimeter and through the transition plane, is greater than 50° and less than or equal to about 85°.

Embodiment F is the article of Embodiment E, wherein the second angle is about 65° to about 75°.

Embodiment G is the article of Embodiment F, wherein the second angle is about 68° to about 72°.

Embodiment H is the article of Embodiment G, wherein the second angle is about 70°.

Embodiment I is the article of any one of the preceding Embodiments, wherein the transition plane is disposed about 60 μm to about 490 μm away from the platform portion when measured along the central axis.

Embodiment J is the article of Embodiment I, wherein the transition plane is disposed about 150 μm to about 350 μm away from the platform portion when measured along the central axis.

Embodiment K is the article of Embodiment J, wherein the transition plane is disposed about 200 μm to about 300 μm away from the platform portion when measured along the central axis.

Embodiment L is the article of Embodiment K, wherein the transition plane is disposed about 250 μm to about 270 μm away from the platform portion when measured along the central axis.

Embodiment M is an article, comprising:
a first side comprising a central cavity portion and a platform portion that projects from the first side and that is not coplanar with the central cavity portion;
a second side opposite the first side; and
at least three hollow microneedles extending from the platform portion in a first direction;
wherein the platform portion substantially surrounds the central cavity portion;
wherein the platform portion comprises an inner perimeter proximate the central cavity portion and an outer perimeter distal the central cavity portion;
wherein each of the at least three hollow microneedles comprises a body that comprises:
an outer surface;
a base segment having a base and a first shape that is defined by a first section of the outer surface;

a tip segment having a tip and a second shape that is defined by a second section of the outer surface, wherein the second shape is distinct from the first shape;

a transition plane that delineates the base segment and the tip segment; and a central axis;

wherein each of the at least three hollow microneedles comprises a height measured from the base to the tip;

wherein the tip segment of each of the at least three hollow microneedle defines at least about 45% of the height of at least one of the at least three hollow microneedles.

Embodiment N is the article of Embodiment M, wherein the tip segment of each of the at least three hollow microneedle defines about 60% to about 85% of the height of at least one of the at least three hollow microneedles.

Embodiment O is the article of Embodiment N, wherein the tip segment of each of the at least three hollow microneedle defines about 70% to about 80% of the height of at least one of the at least three hollow microneedles.

Embodiment P is the article of any one of Embodiments M through O, wherein the base segment is conical-shaped and the tip segment is substantially cylindrical-shaped.

Embodiment Q is the article of any one of Embodiments M through P, wherein the height comprises a first height component associated with the base segment and a second height component associated with the tip segment; wherein the second height component is about 540 μm to about 1240 μm.

Embodiment R is the article of Embodiment Q, wherein the second height component is about 540 μm to about 940 μm.

Embodiment 5 is the article of Embodiment R, wherein the second height component is about 640 μm to about 840 μm.

Embodiment T is the article of Embodiment S, wherein the second height component is about 700 μm to about 800 μm.

Embodiment U is the article of any one of Embodiments Q through T, wherein the first height component is about 250 μm to about 270 μm.

Embodiment V is the article of any one of the preceding Embodiments, wherein the first side further comprises a microneedle-free peripheral portion extending laterally from at least a part of the outer perimeter of the platform portion, wherein the peripheral portion is canted away from the platform portion in a second direction opposite the first direction.

Embodiment W is the article of any one of the preceding Embodiments, wherein the article further comprises a side wall portion that extends from the platform portion or, if present, the peripheral portion; wherein the sidewall portion extends substantially opposite the first direction.

Embodiment X is the article of any one of the preceding Embodiments, wherein the central cavity is a closed cavity.

Embodiment Y is the article of any one of Embodiments A through W, wherein the central cavity is a through-hole extending from the first side through the second side.

Embodiment Z is the article of any one of the preceding Embodiments, wherein the platform is circinate.

Embodiment AA is the article of any one of the preceding Embodiments, wherein the array of microneedles is circinate.

Embodiment AB is the article of any one of the preceding Embodiments, wherein a unitary body comprises the platform portion, the peripheral portion, and the central cavity portion.

Embodiment AC is the article of any one of the preceding Embodiments, wherein at least one microneedle of the plurality comprises:

a base;

an elongated body having a central axis and a body diameter;

a tip portion comprising a tip, a first bevel face oriented diagonally with respect to the central axis and extending through at least 75% of the body diameter, a second bevel face oriented substantially perpendicular to the central axis and intersecting the first bevel face, a bevel opening defined by a first edge of the first bevel face and a second edge of the second bevel face; and a hollow channel that extends axially into the body from the bevel opening.

Embodiment AD is the article of any one of the preceding Embodiments, wherein at least one microneedle of the plurality comprises:

a base;

an elongated body having a central axis;

a tip portion comprising a tip, a beveled surface, and a bevel opening in the beveled surface;

a first channel that extends axially from the bevel opening through at least a portion of the elongated body, wherein the first channel has a first wall that is substantially aligned with the central axis; and a second channel that extends radially from the first channel to the bevel opening, wherein the second channel has a second wall that is oriented substantially orthogonal to the central axis;

wherein the first channel and second channel merge to form the bevel opening.

Embodiment AE is the article of any one of the preceding Embodiments, wherein the at least one microneedle comprises a hollow channel extending through the article from a first opening proximate the tip to a second opening in the second side of the article.

Embodiment AF is the article of any one of the preceding Embodiments, for injecting fluid into a body.

Embodiment AG is the article of any one of Embodiments A through AE, for extracting fluid from a body.

Embodiment AH is an injection and infusion apparatus, comprising:

a hollow-microneedle array article according to any one of the preceding Embodiments;

a hollow-microneedle array article holder;

a first stored energy component configured to move the hollow-microneedle array article from a first position to a second position; and a reservoir containing a fluid, the reservoir being in fluid communication with the hollow microneedles;

wherein the apparatus is configured to propel the article in a predetermined direction at a predetermined velocity.

Embodiment AI is the injection and infusion apparatus of Embodiment AH, wherein the reservoir is configured to hold a volume of fluid of about 0.2 mL to about 5.0 mL.

Embodiment AJ is the injection and infusion apparatus of Embodiment AI, wherein the reservoir is configured to hold a volume of fluid of about 0.2 mL to about 3.0 mL.

Embodiment AK is the injection and infusion apparatus of Embodiment AJ, wherein the reservoir is configured to hold a volume of fluid of about 0.2 mL to about 2.0 mL.

Embodiment AL is the injection and infusion apparatus of Embodiment AK, wherein the reservoir is configured to hold a volume of fluid of about 0.5 mL to about 2.0 mL.

Embodiment AM is the injection and infusion apparatus of any one of Embodiments AH through AL, wherein the predetermined velocity is about 2 m/second to about 20 m/second.

Embodiment AN is the injection and infusion apparatus of Embodiment AM, wherein the predetermined velocity is about 4 m/second to about 12 m/second.

Embodiment AO is the injection and infusion apparatus of Embodiment AN, wherein the predetermined velocity is about 6 m/second to about 9 m/second.

Embodiment AP is the injection and infusion apparatus of Embodiment AO, wherein the predetermined velocity is about 7 m/second to about 8 m/second.

Embodiment AQ is the injection and infusion apparatus of any one of Embodiments AH through AP, further comprising an actuator that actuates movement of the hollow-microneedle array article from the first position to the second position.

Embodiment AR is the apparatus of any one of Embodiments AH through AQ, further comprising a second stored energy component configured to provide a force that moves the fluid from the reservoir to and through the hollow microneedles.

Embodiment AS is a method, comprising:
providing the injection and infusion apparatus of Embodiment AQ or Embodiment AR;
actuating the actuator so as to insert the hollow microneedles through a surface of a skin.

Embodiment AT is the method of Embodiment AS as dependent upon Embodiment AR, further comprising releasing at least a portion of the stored energy of the second stored energy component so as to move fluid from the reservoir through the hollow microneedles and into a tissue below the surface of the skin.

Embodiment AU is the method of Embodiment AS or Embodiment AT, wherein inserting the hollow microneedles through the surface of the skin comprises inserting the hollow microneedles to a depth of about 580 µm to 750 µm below the surface of the skin.

EXAMPLES

Example 1. Fabrication of Microneedle Articles

The microneedle articles were prepared from polymeric material using standard injection molding procedures. The molded microneedle articles were prepared using a mold assembly prepared from three mold sections with each section machined from steel. The first mold section contained projections that defined the beveled shape of the needle tip in the molded array. Each projection in the first mold section had a further cylindrical extension that defined features of the tip segment of the microneedles tip, including the opening on a bevel proximate the tip of the microneedle and a portion of the hollow channel extending through the body of each microneedle. The second mold section served as a template to define the pattern of the microneedles in the molded article, the external shape and size of the microneedles in the molded article, and the first side of the article (including the central cavity portion, platform portion, and peripheral portion, as described above). The third mold section contained cylindrical projections emerging from a planar surface with each projection defining a second (base-proximal) part of the microneedle hollow channel and the opening located at the base of each microneedle in the molded article. The planar surface from which the projections emerged served to define the second major surface of the base segment of the molded article. The first and second mold sections were assembled to form a tight fit by inserting the projections of the first mold section into the corresponding openings in the second mold section. The assembled first and second mold sections formed the first mold half. The third mold section was used as the second mold half.

The first and second mold halves were installed in a mold base in a 20 or 40-ton injection molding press. As is common in the art, the parting line of the mold assembly had both primary and secondary vents for general air evacuation during injection of the polymeric material. Vectra MT1300 liquid crystal polymer (LCP) pellets (Ticona Engineering Polymers, Florence, Ky.) were loaded into a screw and heated until molten.

The first mold half and second mold half were heated to a temperature range (hereafter referred to as the "mold temperature at injection") of about 140-248° F. (60-120° C.). The molding cycle was initiated by closing the first mold half with the second mold half. The molds were clamped together with approximately 20 to 40 tons of force. In the clamped position, the surfaces at the tips of the projections in the second mold half were aligned with and in contact with the surfaces at the tips of the projections in the first mold half. A first portion (approx. 50-99% of the part size volume) of the total amount of material was injected into the mold chamber at a fixed velocity (hereafter referred to as the "injection velocity") of about 7 inches/second (17.8 cm/second). After injecting the first portion of material, the process was switched from an injection-driven to a pressure-driven mode by applying a fixed pressure (hereafter referred to as the "pack pressure") ranging from about 3,000-13,500 psi (20,684-93,079 kilopascal) to force the remainder of the molten material into the negative mold insert. The pack pressure was applied for a fixed time (hereafter referred to as the "hold time") of 2-6 seconds. The pack pressure was subsequently released and the mold chamber was cooled to an ejection temperature set below the softening temperature of LCP. The mold chamber was opened and the microneedle article was ejected.

Example 2. Injection Applicator Used to Test the Microneedle Articles

Fully assembled low-profile microneedle article injection and infusion apparatuses similar to the apparatuses described in International Patent Application Publication No. WO2014/193725 (see FIGS. 1-26) were used. All of the injection and infusion apparatuses were manufactured to the same specifications. The external housing of each injection and infusion apparatus was about 122.8 mm in overall length with a width of about 40.5 mm in the rounded section of the apparatus (section of the apparatus containing the microneedle array holder). The width of the injection and infusion apparatus housing in the elongated section (containing the injection assembly) was about 22.8 mm. The external opening to the cavity of the actuator had a diameter measurement of about 18 mm. The glass cartridge in each injection and infusion apparatus contained a 2 mL solution of 0.005% methylene blue in five percent aqueous dextrose. Each cartridge was about 46 mm in length and had an inner diameter dimension of about 9.7 mm. The first stored energy device used to move the microneedle array holder and insert the microneedles in the skin was a coil spring with a force of 12.5 N in the primed (pre-actuation) state. The second stored energy device used to initiate movement of the shuttle was a coil spring with a force of 16.5 N in the primed (pre-actuation) state. The third stored energy device used to infuse the methylene blue dye was a coil spring with a force of 15 N in the primed (pre-actuation) state. Using the injection and infusion apparatus described herein, the velocity of the microneedles at the surface of the skin was about 7.4±1.4 m/sec.

The hollow microneedle article (as shown in FIG. 1) used in the microneedle article injection and infusion apparatus was molded (as described in Example 1) from Vectra MT1300 liquid crystal polymer (LCP) in the shape of a circle approximately 1.25 cm in diameter (dimension D3 of FIG. 8). The circular platform portion projected about 1.0 mm from the outside edge of the article (Height $H_1$ of FIG. 2) and the peripheral portion canted away from the platform portion with a 36.9 degree cant, relative to the plane of the platform portion. The closed circular cavity of the article was centered on the article with a diameter of about 6.8 mm (diameter measurement D1 (FIG. 8) defined by the circular region formed by the inner perimeter of the platform), a depth of about 500 microns at the center of the cavity, and a radius of curvature of about 11 mm. The diameter of the circular region formed by the outer perimeter of the platform was about 10.3 mm (dimension D2 in FIG. 8). The width of the platform was about 1.75 mm (dimension D4 in FIG. 8). The article featured an array of 12 hollow microneedles extending from the circular platform portion of the article. The microneedles were evenly spaced with the distance between neighboring microneedles being about 2.2 mm (as measured from tip to tip). Each microneedle was oriented so that the opening at the tip was facing toward the outer perimeter of the article along a radial vector. The external diameter of each microneedle at the base was about 0.45 mm. The flared base segment of each microneedle had a radius of curvature of about 1 mm. The tip segment of each microneedle was in the shape of a conventional hypodermic needle with a bevel of about 25 degrees and a chamfered tip that had an included angle of 70 degrees. The opening near the tip was obround in shape (as shown in FIG. 2A) with dimensions of about 200 microns by 80 microns. Each microneedle had a total height of about 1000 microns as measured from the base of the microneedle at the platform surface to the tip of the microneedle. The length of the tip segment (as measured from the tip to the transition plane that delineated the flared base segment from the substantially cylindrical tip segment, FIG. 2A) was about 739 microns. The external diameter at the midpoint of the tip segment was about 254 microns. The distance from the tip of each microneedle to the center of the opening near the tip was about 270 microns. The average diameter of the hollow channel through the tip segment of each microneedle was about 80 microns. The angle theta ($8i$, as shown in FIG. 5A) was 70.0 degrees.

Example 3. Use of Microneedle Article to Inject a Substance

The study was conducted using Yorkshire cross domestic pigs (Midwest Research Swine; Gibbon, Minn.) in vivo. The ham region was selected as the application site for microneedle insertion. The application site was first trimmed with an electric clipper and then shaved using a razor and shaving cream. The shaved area was scrubbed using soapy water and a BUF-PUF exfoliation sponge (3M Company, St. Paul, Minn.) and then rinsed with deionized water. The animal was placed in a lateral recumbent position on a heated table (38° C.). The animal was anesthetized with isofluorene gas and maintained under anesthesia throughout the experiment. The application site was then wiped with a 70% isopropanol in water solution.

The injection apparatus of Example 2 was used. The release liner was removed from the skin contact adhesive portion of the apparatus was adhered to the skin of the pig. The apparatus was actuated to cause sequential release of the array holder element, insertion of the microneedles of the microneedle article into the skin of the pig, and injection of the methylene blue solution into the pig. After completion of the injection, the apparatus was maintained on the skin for one additional minute. The time required to inject the entire sample into the animal was recorded. The apparatus was removed from the skin and the skin surface was examined to determine if there was any methylene blue solution on the surface of the skin. The presence of methylene blue solution on the skin was an indication that not all of the methylene blue was injected into the animal. The remainder of the methylene blue solution remained in the cartridge. The results are presented in Table 1.

A total of ten replicates were conducted. The injection times ranged from 94 to 237 seconds with the average injection time being 157 seconds. In nine of the tests, all of the methylene blue solution was injected into the animal. In one test, 98.9% of the methylene blue solution was injected into the animal.

TABLE 1

Injection Time (Example 3).

| Test Number | Injection Time (seconds) | Percentage of Methylene Blue Injected |
| --- | --- | --- |
| 1 | 183 | 100 |
| 2 | 185 | 100 |
| 3 | 237 | 100 |
| 4 | 185 | 100 |
| 5 | 207 | 100 |
| 6 | 111 | 100 |
| 7 | 148 | 100 |
| 8 | 119 | 100 |
| 9 | 99 | 98.9 |
| 10 | 94 | 100 |

Example 4. Use of Microneedle Article

A study was conducted to determine the depth of penetration (DOP) of the microneedles of the article when applied to the skin surface of a Yorkshire cross domestic pigs (Midwest Research Swine), in vivo. The hollow microneedle article described in Example 2 was used.

The microneedles on the article were coated using a three step process. The first two steps involved applying primer coatings to the microneedles and the third step involved applying a thin coating of Rhodamine B to the microneedles. In Step 1, the articles were flood coated with a 35 microliter solution containing 0.5 mg/mL polyvinyl alcohol (80% hydrolyzed) (Sigma-Aldrich, Inc., St. Louis, Mo.) and 35 µg/ml of TWEEN® 80 (Sigma-Aldrich) in 90% (w/v) ethanol. The coated articles were then dried at 35° C. for 20 minutes. In Step 2, the articles from Step 1 were flood coated with 35 microliters of an aqueous solution of 33.3 mg/ml aluminum potassium sulfate (Penta Manufacturing, Livingston, N.J.). The coated articles were then dried at 35° C. for 30 minutes. In Step 3, the primed articles from Step 2 were flood coated with 40 microliters of an aqueous solution of 0.08% (w/v) Rhodamine B (Sigma-Aldrich). The coated articles were dried at 35° C. for 30 minutes. The three step process provided articles in which the microneedles were completely covered with a thin, opaque coating of Rhodamine B.

The ham region was selected as the application site for microneedle insertion. The application site was first trimmed with an electric clipper and then shaved using a razor and shaving cream. The shaved area was scrubbed using soapy water and a BUF-PUF exfoliation sponge (3M Company) and then rinsed with deionized water. The animal was placed in a lateral recumbent position on a heated table (38° C.). The animal was anesthetized with isofluorene gas and maintained under anesthesia throughout the experiment. The application site was then wiped with a 70% isopropanol in water solution.

The injection apparatus described in Example 2 with a Rhodamine B coated article was used. The only exception was that a blank cartridge was used, instead of a cartridge filled with methylene blue. The release liner was removed from the skin contact adhesive portion of the apparatus and the apparatus was the adhered to the skin of the pig. The apparatus was actuated to cause release of the array holder element and insertion of the microneedles of the microneedle article into the skin of the pig. The injection apparatus was maintained on the skin for an additional 5 minutes.

The injection apparatus was removed from the animal. The depth of penetration (DOP) of the microneedles into the pig skin was determined indirectly by measuring the distance from the tip of the microneedle to where the Rhodamine B coating was wiped or dissolved from the microneedle after application into the skin. The measurement was conducted using a Nikon LV-100 microscope at 100× magnification (Nikon Instruments, Melville, N.Y.) with Image Pro® Plus digital image analysis software (Media Cybernetics, Bethesda, Md.). A total of five microneedle articles were tested. The mean microneedle DOP was determined by sampling all of the microneedles from each article (n=60). The results are presented in Table 2.

TABLE 2

Depth of Penetration (DOP) when Microneedle Article was Applied to the Ham Area (Example 4)

| | |
|---|---|
| Mean DOP | 665 microns |
| Standard Deviation | 80 microns |
| % RSD | 12% |

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Various modifications may be made without departing from the spirit and scope of the invention. These and other embodiments are within the scope of the following claims.

The invention claimed is:

1. An article, comprising:
    a first side comprising a central cavity portion and a platform portion that projects from the first side and that is not coplanar with the central cavity portion;
    a second side opposite the first side; and
    at least three hollow microneedles extending from the platform portion in a first direction;
    wherein the platform portion substantially surrounds the central cavity portion;
    wherein the platform portion comprises an inner perimeter proximate the central cavity portion and an outer perimeter distal the central cavity portion;
    wherein the at least three hollow microneedles each comprise an elongated body that comprises:
        an outer surface;
        a base segment having a base and a first shape that is defined by a first section of the outer surface;
        a tip segment having a tip and a second shape that is defined by a second section of the outer surface, wherein the second shape is distinct from the first shape;
        a transition plane that delineates the base segment and the tip segment; and
        a central axis;
    wherein a first angle, defined by the central axis of each of the at least three hollow microneedles and a shortest line extending from the outer perimeter of the platform portion and through the transition plane of the microneedle, is greater than 50° and less than or equal to about 85°.

2. The article of claim 1, wherein the first angle is about 65° to about 75°.

3. The article of claim 1, wherein a second angle, defined by the central axis and a shortest line extending from the inner perimeter and through the transition plane, is greater than 50° and less than or equal to about 85°.

4. The article of claim 1, wherein the transition plane is disposed about 60 µm to about 490 µm away from the platform portion when measured along the central axis.

5. The article of claim 1, wherein the first side further comprises a microneedle-free peripheral portion extending laterally from at least a part of the outer perimeter of the platform portion, wherein the peripheral portion is canted away from the platform portion in a second direction opposite the first direction.

6. The article of claim 5, wherein a unitary body comprises the platform portion, the peripheral portion, and the central cavity portion.

7. The article of claim 1; wherein the article further comprises a side wall portion that extends from the platform portion; wherein the sidewall portion extends substantially opposite the first direction.

8. The article of claim 1, wherein the central cavity portion is a closed cavity.

9. The article of claim 1, wherein the central cavity portion is a through-hole extending from the first side through the second side.

10. The article of claim 1, wherein at least one microneedle of the at least three hollow microneedles comprises:
    the elongated body having an elongated body diameter;
    a tip portion of the tip segment, wherein the tip portion comprises the tip, a first bevel face oriented diagonally with respect to the central axis and extending through at least 75% of the elongated body diameter, a second bevel face oriented substantially perpendicular to the central axis and intersecting the first bevel face, a bevel opening defined by a first edge of the first bevel face and a second edge of the second bevel face; and a hollow channel that extends axially into the elongated body from the bevel opening.

11. The article of claim 1, wherein at least one microneedle of the at least three hollow microneedles comprises:

tip portion of the tip segment, wherein the tip portion comprises the tip, a beveled surface, and a bevel opening in the beveled surface;

a first channel that extends axially from the bevel opening through at least a portion of the elongated body, wherein the first channel has a first wall that is substantially aligned with the central axis; and a second channel that extends radially from the first channel to the bevel opening, wherein the second channel has a second wall that is oriented substantially orthogonal to the central axis;

wherein the first channel and second channel merge to form the bevel opening.

12. The article of claim 1, wherein the at least one microneedle comprises a hollow channel extending through the article from a first opening proximate the tip to a second opening in the second side of the article.

13. An injection and infusion apparatus, comprising:

a hollow-microneedle array article according to claim 1;

a hollow-microneedle array article holder;

a first stored energy component configured to move the hollow-microneedle array article from a first position to a second position; and a reservoir containing a fluid, the reservoir being in fluid communication with the at least three hollow microneedles;

wherein the apparatus is configured to propel the article in a predetermined direction at a predetermined velocity.

14. The apparatus of claim 13, wherein the predetermined velocity is about 2 m/second to about 20 m/second.

15. The apparatus of claim 13, further comprising an actuator that actuates movement of the hollow-microneedle array article from the first position to the second position.

16. A method, comprising:

providing the injection and infusion apparatus of claim 15;

actuating the actuator so as to insert the at least three hollow microneedles through a surface of a skin.

17. The apparatus of claim 13, further comprising a second stored energy component configured to provide a force that moves the fluid from the reservoir to and through the at least three hollow microneedles.

18. A method, comprising:

providing the injection and infusion apparatus of claim 17;

actuating the actuator so as to insert the at least three hollow microneedles through a surface of a skin.

* * * * *

UNITED STATES PATENT AND TRADEMARK OFFICE
CERTIFICATE OF CORRECTION

PATENT NO.         : 10,398,885 B2
APPLICATION NO.    : 15/545029
DATED              : September 3, 2019
INVENTOR(S)        : Michael J. Frits It is certified that error appears in the above-identified patent and that said Letters Patent is hereby corrected as shown below:

In the Specification

Column 4
Line 41, Delete "83" and insert -- $\Theta_3$ --, therefor.

Column 5
Line 67, Delete "circulate" and insert -- circinate --, therefor.

Column 13
Line 34, Delete "entirety" and insert -- entirety. --, therefor.

Column 19
Line 33, Delete "5" and insert -- S --, therefor.

Column 23
Line 51, Delete "(8i," and insert -- ($\theta_1$, --, therefor.
Line 67, Delete "isofluorene" and insert -- isoflurane --, therefor.

Column 25
Line 12, Delete "isofluorene" and insert -- isoflurane --, therefor.

In the Claims

Column 27
Line 9, In Claim 11, before "tip" insert -- a --.

Signed and Sealed this
Twenty-second Day of October, 2019

Andrei Iancu
*Director of the United States Patent and Trademark Office*